United States Patent
Gutermuth et al.

(10) Patent No.: US 6,884,324 B2
(45) Date of Patent: Apr. 26, 2005

(54) COLUMN FOR CONCENTRATING PHTHALIC ANHYDRIDE

(75) Inventors: Thomas Gutermuth, Maintal (DE); Helmuth Domes, Obertshausen (DE)

(73) Assignee: Lurgi AG, Frankfurt am Main (DE)

( * ) Notice: Subject to any disclaimer, the term of this patent is extended or adjusted under 35 U.S.C. 154(b) by 61 days.

(21) Appl. No.: 10/348,391

(22) Filed: Jan. 21, 2003

(65) Prior Publication Data
US 2003/0139611 A1 Jul. 24, 2003

(30) Foreign Application Priority Data
Jan. 22, 2002 (DE) .......................... 102 07 460

(51) Int. Cl.[7] .............................. B01D 3/10; B01D 3/14; C07D 307/89
(52) U.S. Cl. ...................... 202/153; 202/156; 202/205; 202/267.1; 203/80; 203/86; 549/247; 549/250
(58) Field of Search ................................ 202/152–156, 202/205, 267.1; 203/73, 78, 80, 86; 196/111; 549/247, 250

(56) References Cited

U.S. PATENT DOCUMENTS

| | | | | |
|---|---|---|---|---|
| 2,031,336 A | * | 2/1936 | Van Tonningen | 208/76 |
| 2,149,943 A | * | 3/1939 | Smith | 196/55 |
| 4,629,534 A | * | 12/1986 | Ezell | 203/98 |
| 5,200,040 A | * | 4/1993 | Naka et al. | 203/25 |
| 6,077,985 A | * | 6/2000 | Stork | 585/800 |
| 6,558,515 B1 | * | 5/2003 | Steacy | 203/1 |

* cited by examiner

Primary Examiner—Virginia Manoharan
(74) Attorney, Agent, or Firm—Norris McLaughlin & Marcus PA

(57) ABSTRACT

To improve the columns used so far for producing phthalic anhydride, and to make them less expensive and easier to install, it is proposed that in the column for concentrating phthalic anhydride two distillation stages are arranged, wherein the removal of the low-boiling components of the crude phthalic anhydride by distillation is effected in the first distillation stage (2) and the separation of the high-boiling components from the pure phthalic anhydride is effected in the second distillation stage (3), both distillation stages being arranged side by side and being separated from each other by a vertical wall (4), and that the bottom (7) of the first distillation stage (2) is connected with the bottom (10) of the second distillation stage (3).

14 Claims, 1 Drawing Sheet

COLUMN FOR CONCENTRATING PHTHALIC ANHYDRIDE

This invention relates to a distillation column for producing phthalic anhydride.

BACKGROUND OF THE INVENTION

Crude phthalic anhydride contains a number of lower- and higher-boiling byproducts such as benzoic acid, maleic anhydride, phthalide, etc., which for reasons of the requirements as to the quality of the pure phthalic anhydride must be removed as far as possible. Up to now, crude phthalic anhydride is liberated from lower-boiling byproducts in a first distillation stage. In a second distillation stage, high-boiling components are separated, and pure phthalic anhydride is recovered as top product.

The distillation of the crude phthalic anhydride has so far been performed as follows: As a result of gravimetric level differences, the crude phthalic anhydride coming from the thermal pretreatment (where water is removed and/or phthalic acid is converted to phthalic anhydride) gets into the so-called pretreatment column, where the crude phthalic anhydride is introduced in liquid form between the uppermost tray and the overlying structured packing and is expanded into the column. In the bottom of the pretreatment column, the crude phthalic anhydride is evaporated. The ascending vapors undergo a mass transfer with the liquid trickling down from the inlet of crude phthalic anhydride or of the top condenser. From the top condensate, in which the lower-boiling byproducts (together with phthalic anhydride) are concentrated, a small part is withdrawn and delivered as waste to the so-called residue container. Thus, the bottom in the pretreatment column is liberated from low-boiling components. The boiling liquid in the bottom is gravimetrically supplied to the bottom of the pure-phthalic-anhydride column. This is effected by means of an overflow. This column operates as pure enriching column and is equipped with 20 valve trays. At the top of the pure-phthalic-anhydride column the pure phthalic anhydride is withdrawn and in part supplied as reflux to the upper tray. The other part is withdrawn as pure product. The bottom residue of the column (high-boiling components) is withdrawn from the column and discontinuously heated to about 250° C. in a boiling vessel, so as to recover phthalic anhydride contained therein by evaporation. Performing the distillation by means of such apparatus has been quite successful for decades, but has the disadvantage that two complete columns are required. This involves not only high investment costs, but also the necessary space requirement for the associated steel construction. Both columns operate under a vacuum of about 140 mbar and have separate vacuum systems.

Columns for concentrating phthalic anhydride are described for instance in DE-A-3538911. There are used two distillation columns arranged side by side for producing e.g. phthalic anhydride. EP-B-0087678 describes a very high tray column, likewise for purifying phthalic anhydride. There are likewise known columns which by means of a partition are divided into partial regions of the column, in order to avoid the cross-mixing of liquid or vapor streams. This is described in DE-A-3522234. In DE-A-4336986 a column is described, which is divided over the entire cross-section by means of a baffle plate. In this column, one mass transfer package each is arranged in both column halves. Both columns are not suitable for producing phthalic anhydride.

Proceeding from this prior art, it is the object underlying the invention to improve the previous column arrangement in terms of apparatus and make it less expensive and easier to install.

SUMMARY OF THE INVENTION

In accordance with the invention, this object is solved in the above-mentioned column in that two distillation stages are disposed in the column for concentrating phthalic anhydride, wherein the removal of the low-boiling components in the crude phthalic anhydride by distillation is effected in the first distillation stage and the separation of the high-boiling components from the pure phthalic anhydride is performed in the second distillation stage, both distillation stages being arranged side by side and being separated from each other by a vertical wall, and wherein the bottom of the first distillation stage is connected with the bottom of the second distillation stage.

DETAILED DESCRIPTION

In the following description, the first distillation stage is referred to as primary column, and the second distillation stage is referred to as phthalic-anhydride column.

Since even in the version with two separate columns the bottom outlet of the primary column and the bottom inlet of the phthalic-anhydride column have the same composition and both bottoms virtually have the same pressures and temperatures, the bottom of the primary column can directly be passed on into the bottom of the phthalic-anhydride column by means of an overflow pipe. The previous gravimetric delivery of the bottom of the primary column into the bottom of the phthalic-anhydride column can thus be omitted.

Since the primary column and the pure-phthalic-anhydride column are operated with different boiling rates, both stages of the baffle-plate column must each be equipped with one boiler and one top condenser.

The condensers are fed via a common water inlet and water outlet.

Embodiments of the column will be explained by way of example with reference to the drawing.

Figure 1:
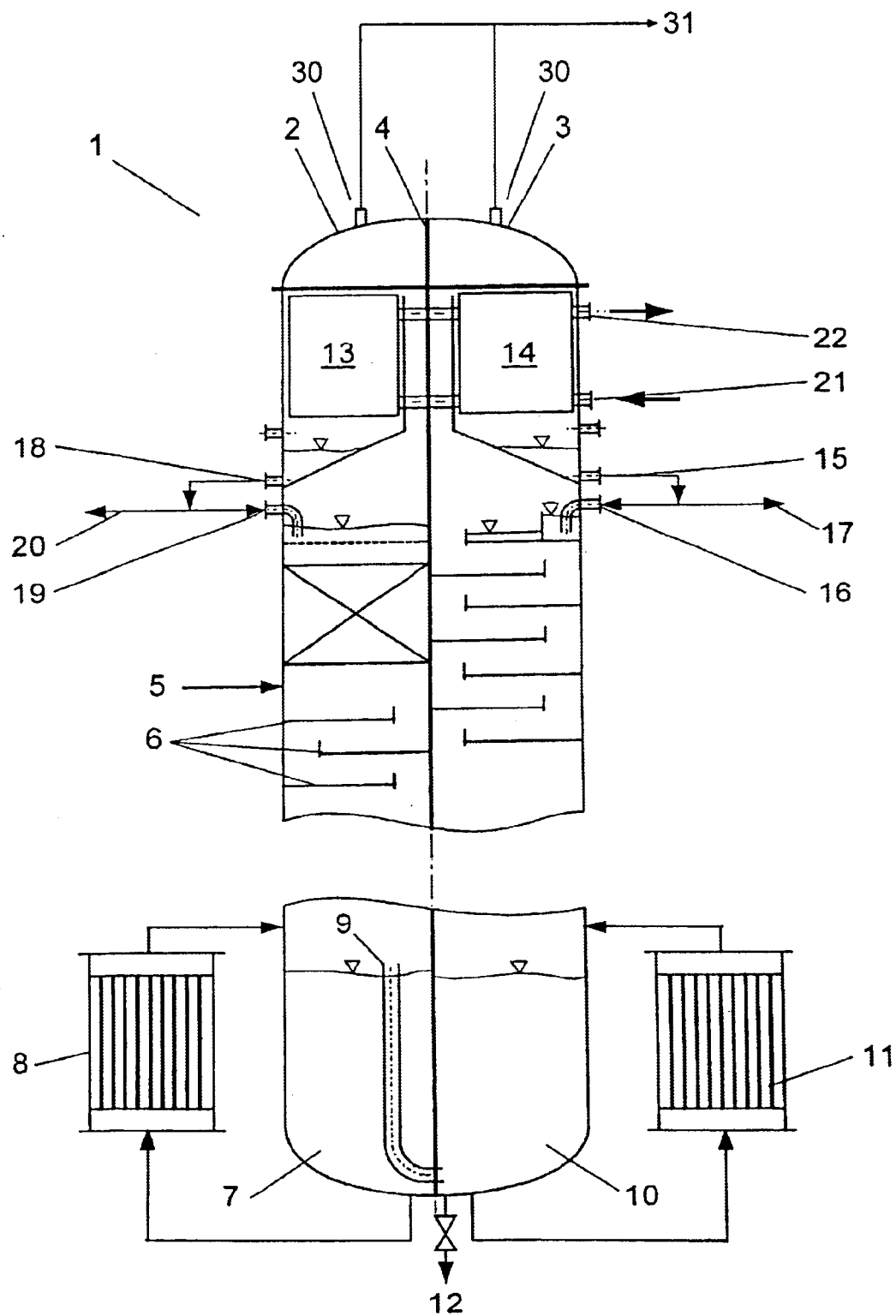
FIG. 1 illustrates the distillation column of the invention.

In the inventive modification of the distillation of crude phthalic anhydride, a so-called partition column (1) is being used instead of the two separate columns, which partition column technically performs the same function as the two separate columns. Along its entire length, including the trays as well as bottom and top, the cylindrical column body of the partition column (1) is divided into two semicircular segments by means of a wall (4). The wall (4) may be made of stainless steel sheet or other chemically resistant materials, which can absorb the load produced by temperature and pressure. On the left side of the drawing, the primary column (2) is shown, and on the right side the pure-phthalic-anhydride column (3) is shown. In the primary column (2), the distillation of the crude phthalic anhydride (first distillation stage) is effected, and in the pure-phthalic-anhydride column (3) the distillation of the pure phthalic anhydride (second distillation stage) is effected.

The liquid crude phthalic anhydride (5) coming from the thermal pretreatment is expanded into the primary column (2). The vapors produced ascend in the primary column (2), while the liquid portion of the expanded phthalic anhydride trickles into the bottom (7) of the primary column (2) via the valve trays (6). Boiling up the bottom (7) is effected by means of a circulation boiler (8). Since even in the version with two separate columns, the bottom outlet of the primary column (2) and the bottom inlet of the pure-phthalicanhydride column (3) have the same composition and both bottoms virtually have the same pressures and temperatures, the bottom (7) of the primary column can directly be passed on into the bottom of the phthalic-anhydride column (10) by means of an overflow pipe (9). Alternatively, the liquid can also be delivered by means of a pump.

The phthalic anhydride in the bottom (10) of the phthalic-anhydride column (3) is boiled up by means of a circulation boiler (11) and is recondensed as pure phthalic anhydride at the top of the phthalic-anhydride column (3) by means of a condenser (14), one part flowing back as reflux through line (15) and line (16) into the phthalic-anhydride column (3) and the other part being recovered as pure product (17). In the column bottom (10) heavy-boiling components are accumulated, which are discharged continuously into the boiling vessel through line (12).

In the top of the primary column (2), low-boiling components are recondensed by means of the condenser (13), which low-boiling components are in part again introduced as reflux into the primary column (2) through line (18) and line (19) at the top of the column, and a small part of which is collected as residue via line (20).

In the top of the primary column (2) and in the top of the phthalic-anhydride column (3), there is each disposed a condenser (13, 14), which condensers are supplied with feed water via a common inlet (21) and outlet (22); the condensation heat obtained on the part of the product is utilized for generating steam.

The use of a partition (4) is possible for this application of distillation, as on both sides of the partition column (1) almost the same temperature and pressure conditions exist:

Primary column:

| Temperature: | bottom: 228° C. | top: 200° C. |
| Pressure: | bottom: 0.24 bar abs | top: 0.14 bar abs |

Phthalic-anhydride column:

| Temperature: | bottom: 228° C. | top: 211° C. |
| Pressure: | bottom: 0.24 bar abs | top: 0.14 bar abs |

Thus, only little mechanical loads acting on the partition as a result of differences in pressure and temperature are to be expected.

To be able to operate the partition column under vacuum conditions, suction ports (30) for the non-condensable vapors are provided at the top of the column. Each column side is equipped with a separate port. For both columns, a common vacuum system (31) is being used.

We claim:

1. A column for concentrating phthalic anhydride, comprising two distillation stages disposed side by side to each other within a single column, a partition separating said two distillation stages, wherein removal of low-boiling components in a crude phthalic anhydride is effected in a first distillation stage (2) and separation of high-boiling components from the purified phthalic anhydride is performed in a second distillation stage (3), and an overflow pipe or a pump disposed for connecting the bottom (7) of the first distillation stage (2) with the bottom (10) of the second distillation stage (3).

2. The column as claimed in claim 1, wherein the bottom (7) of the first distillation stage (2) is connected with the bottom (10) of the second distillation stage (3) by an overflow pipe (9).

3. The column as claimed in claim 1, wherein the bottom (7) of the first distillation stage (2) is connected with the bottom (10) of the second distillation stage (3) by a pump.

4. The column as claimed in claim 1, wherein both distillation stages are provided with vacuum by a common vacuum system.

5. The column as claimed in claim 1, wherein the partition (4) is made of sheet metal.

6. The column as claimed in claim 1, wherein both distillation stages are provided with circulation boilers.

7. The column as claimed in claim 1, wherein both distillation stages are provided with condensers.

8. A method for concentrating phthalic anhydride, which comprises distilling crude phthalic anhydride in a first distillation stage of a distillation column having two side-by-side distillation stages, each having a top and bottom and being separated from each other by a partition, to remove lower boiling components from said crude phthalic anhydride, to produce a crude phthalic anhydride product from which lower boiling components have been removed, in the bottom of said first distillation stage, transferring said crude phthalic anhydride product from which lower boiling components have been removed from the bottom of said first distillation stage to the bottom of the second of said two distillation stages, through a connection between said bottoms, and distilling said crude phthalic anhydride product from which said lower boiling components have been removed, in said second distillation stage, to remove higher boiling components therefrom.

9. The method of claim 8, wherein the bottom of the first distillation stage is connected with the bottom of the second distillation stage by an overflow pipe.

10. The method of claim 8, wherein the bottom of the first distillation stage is connected with the bottom of the second distillation stage by a pump.

11. The method of claim 8, wherein both column stages are operated under a vacuum, and that vacuum is provided by a common vacuum system.

12. The method of claim 8, wherein said partition is made of sheet metal.

13. The method of claim 8, wherein each of said two stages are provided with a circulation boiler.

14. The method of claim 8, wherein each of said two stages are provided with a condenser.

* * * * *